US011969198B2

(12) United States Patent
Ellman et al.

(10) Patent No.: US 11,969,198 B2
(45) Date of Patent: Apr. 30, 2024

(54) MALLEABLE ELECTROSURGICAL INSTRUMENT

(71) Applicant: Elliquence, Baldwin, NY (US)

(72) Inventors: Alan Ellman, Hewlett, NY (US); Spencer Ellman, New York, NY (US)

( * ) Notice: Subject to any disclaimer, the term of this patent is extended or adjusted under 35 U.S.C. 154(b) by 218 days.

(21) Appl. No.: 16/821,887

(22) Filed: Mar. 17, 2020

(65) Prior Publication Data

US 2020/0305949 A1    Oct. 1, 2020

Related U.S. Application Data

(60) Provisional application No. 62/824,204, filed on Mar. 26, 2019.

(51) Int. Cl.
*A61B 18/14* (2006.01)
*A61B 18/04* (2006.01)
*A61B 18/00* (2006.01)

(52) U.S. Cl.
CPC .... *A61B 18/04* (2013.01); *A61B 2018/00059* (2013.01); *A61B 2018/0091* (2013.01); *A61B 2018/1467* (2013.01)

(58) Field of Classification Search
CPC ... B25G 1/02; A61B 2018/0091; A61B 18/08; A61B 1/00066; A61B 1/00071; A61B 1/005; A61B 1/0052; A61B 1/0058; A61B 17/2816; A61B 17/2841; A61B 2017/2845; A61B 17/2804; A61B 2017/294; A61B 18/04; A61B 2018/00059; A61B 2018/1475; A61B 18/148; A61B 17/00234; A61B 17/2909; A61B 17/29; A61B 2017/2947; A61B 2017/0042; A61B 2017/0046; A61B 2017/00862; A61B 2017/00867; A61B 2017/00946; A61B 18/082; A61B 18/085; A61B 18/14; A61B 18/1402; A61B 18/1442; A61B 18/1445; A61B 18/1447; A61B 2018/0094; A61B 2018/126; A61B 2018/00339; A61B 2018/00196; A61B 2018/00202; A61B 2018/00607; A61B 2018/00946; A61B 2017/00367; A61B 2017/00371; A61B 2017/00424; A61B 2017/00429; A61B 90/03; A61M 25/0141; A61M 25/0138
USPC ......................... 606/41, 46, 51, 52, 205–208
See application file for complete search history.

(56) References Cited

U.S. PATENT DOCUMENTS

| | | | | |
|---|---|---|---|---|
| 4,726,370 A * | 2/1988 | Karasawa | ............... | A61B 18/14 600/105 |
| 4,955,884 A * | 9/1990 | Grossi | ................ | A61B 18/1485 606/46 |
| 5,147,378 A * | 9/1992 | Markham | ............... | A61B 17/29 294/100 |
| 6,409,728 B1 * | 6/2002 | Ehr | ..................... | A61B 18/1445 606/205 |
| 6,991,633 B2 * | 1/2006 | Agbodoe | ............ | A61B 17/1611 606/170 |
| 7,905,882 B1 * | 3/2011 | Ellman | ............... | A61B 18/1477 606/41 |

(Continued)

*Primary Examiner* — Thomas A Giuliani (57) ABSTRACT

An electrosurgical handpiece is provided that includes a squeezable handle. The squeezable handle has a back grip and a finger grip that can be squeezed to actuate electrosurgical handpiece. The back grip and the finger grip are connected by a lower malleable region that has an elasticity greater than the remainder of the squeezable handle.

18 Claims, 7 Drawing Sheets

(56) References Cited

U.S. PATENT DOCUMENTS

| | | | | |
|---|---|---|---|---|
| 2005/0192592 A1* | 9/2005 | Butler | ............... | A61B 17/221 606/114 |
| 2005/0277917 A1* | 12/2005 | Garito | ............... | A61B 18/1482 606/49 |
| 2007/0032810 A1* | 2/2007 | Storz | ............... | A61B 17/2909 606/174 |
| 2009/0228054 A1* | 9/2009 | Hoffman | ............ | A61B 17/7086 606/86 A |
| 2016/0135880 A1* | 5/2016 | Ellman | ............... | A61B 18/148 606/41 |
| 2016/0331484 A1* | 11/2016 | Ellman | ............. | A61B 18/1482 |
| 2017/0333118 A1* | 11/2017 | Ellman | ............. | A61B 18/1482 |

* cited by examiner

MALLEABLE ELECTROSURGICAL INSTRUMENT

CROSS-REFERENCE TO RELATED APPLICATION

This application claim priority to provisional application No. 62/824,204, the contents of which are incorporated by reference in its entirety.

BACKGROUND

In the field of MIS (minimally invasive surgery) there is a limited ability to maneuver electrosurgical or other instruments in the patient or surgical field. More specifically, during surgery, the surgeon has to maneuver an instrument such as an electrosurgical instrument in a very narrow and sometimes in an obscured optical field. For example, when conducting spinal surgery, the surgeon passes an electrode attached to the electrosurgical instrument through a small passage made in the skin of the patient, muscle and then through various components of the spine including vertebrae to reach the desired region for treatment.

Further, the surgeon must rotate and maneuver the electrosurgical electrode to accurately reach the desired component or target region with the electrosurgical instrument. As such, this placement and maneuvering requires extreme skill and care on behalf of the surgeon to ensure that the surgical instrument is placed in the right location and moved in the right directions.

SUMMARY

An electrosurgical handpiece is provided that includes a squeezable handle. The squeezable handle has a back grip and a finger grip that can be squeezed to actuate electrosurgical handpiece. The backgrip and the finger grip is connected to the back grip by a lower malleable region that has an elasticity greater than the remainder of the squeezable handle.

DETAILED DESCRIPTION OF PREFERRED EMBODIMENTS

Figure 1:
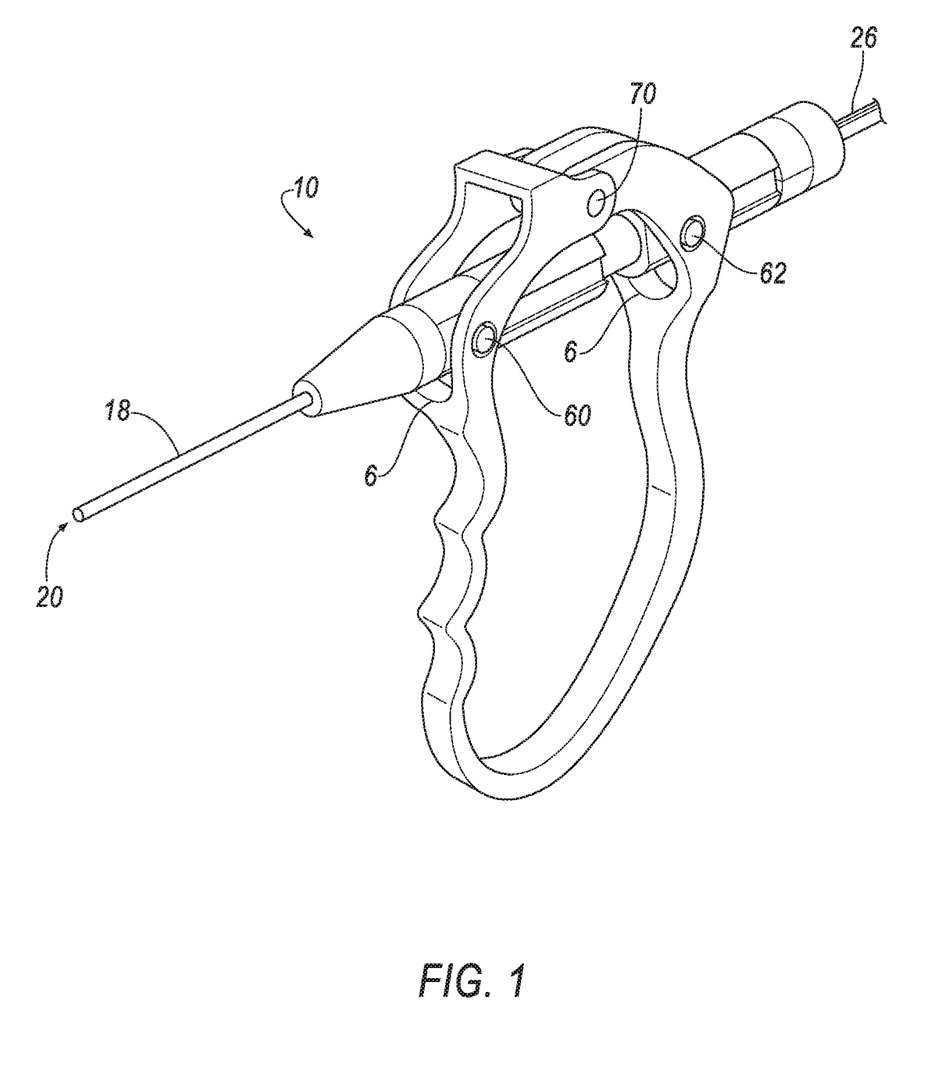
FIG. 1 is a perspective view of a malleable electrosurgical instrument according to one aspect of the invention.
Figure 2:
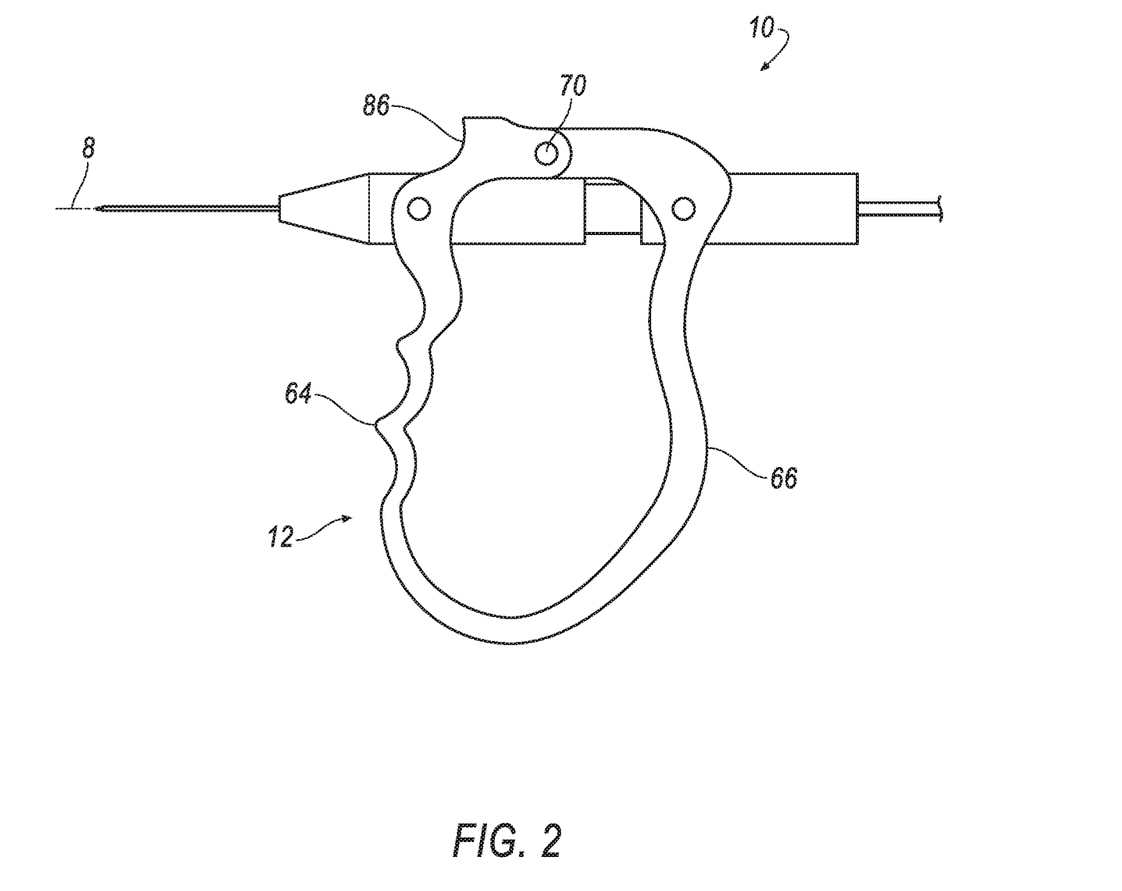
FIG. 2 is a plan view of a malleable electrosurgical instrument according to one aspect of the invention.

The present application incorporates U.S. Pat. No. 7,905,882 entitled Activator for Electrosurgical Handpiece filed May 3, 2007 by reference in its entirety. FIGS. 1 and 2 show one form of electrosurgical handpiece 10 of the invention. One aspect of the invention comprises a squeezable handle 12 assembly connected to and across two front 14 and rear 16 main slideable coaxially-aligned body parts enclosing an elongated outer tubular housing 18 from whose distal end 20 an inner electrode 22 with adjacent active bipolar tips can be extended and retracted when the handle 12 is squeezed or released, respectively. The handpiece common axis is designated 8 in FIG. 2. The handle 12 assembly comprises a front handle part 64 and a rear handle part 66 axially spaced from the former, both of which extend below the axis 8 of the handpiece when the latter is held in its upright position as illustrated in FIG. 2. The upper end of each handle part bifourcated 6 just below its respective pivot point 60, 62, and then the bifurcated handle parts extend upward above the axis 8. At the right end an electrical cord 26 is terminated in a plug connector (not shown). Internally of the handpiece, wires of the electrical cord 26 are connected to the active electrode 22. The outer tubular housing 18 extends from the front at the left completely through the center of the front body part 14 and into the coaxially-aligned rear body part 16 and terminates in the latter. The front body part 14 contains a bore which houses a compression spring engaged by a reduced diameter projecting member of the rear body part 16. The compression spring biases apart the two body parts 14, 16. The handle 12 keeps the body parts 14, 16 from relatively axially rotating. The front body part 14 also has a forwardly-projecting cylindrical collet containing several longitudinal slits (not shown). Onto the forwardly-projecting collet is mounted a nose piece 42 with an internal tapered bore (not shown) which is configured to cooperate in the conventional manner with the collet so that when the nose piece is forced onto the forwardly-projecting collet, the collet part closes along the slits and locks to the outer tubular housing 18.

Figure 3:
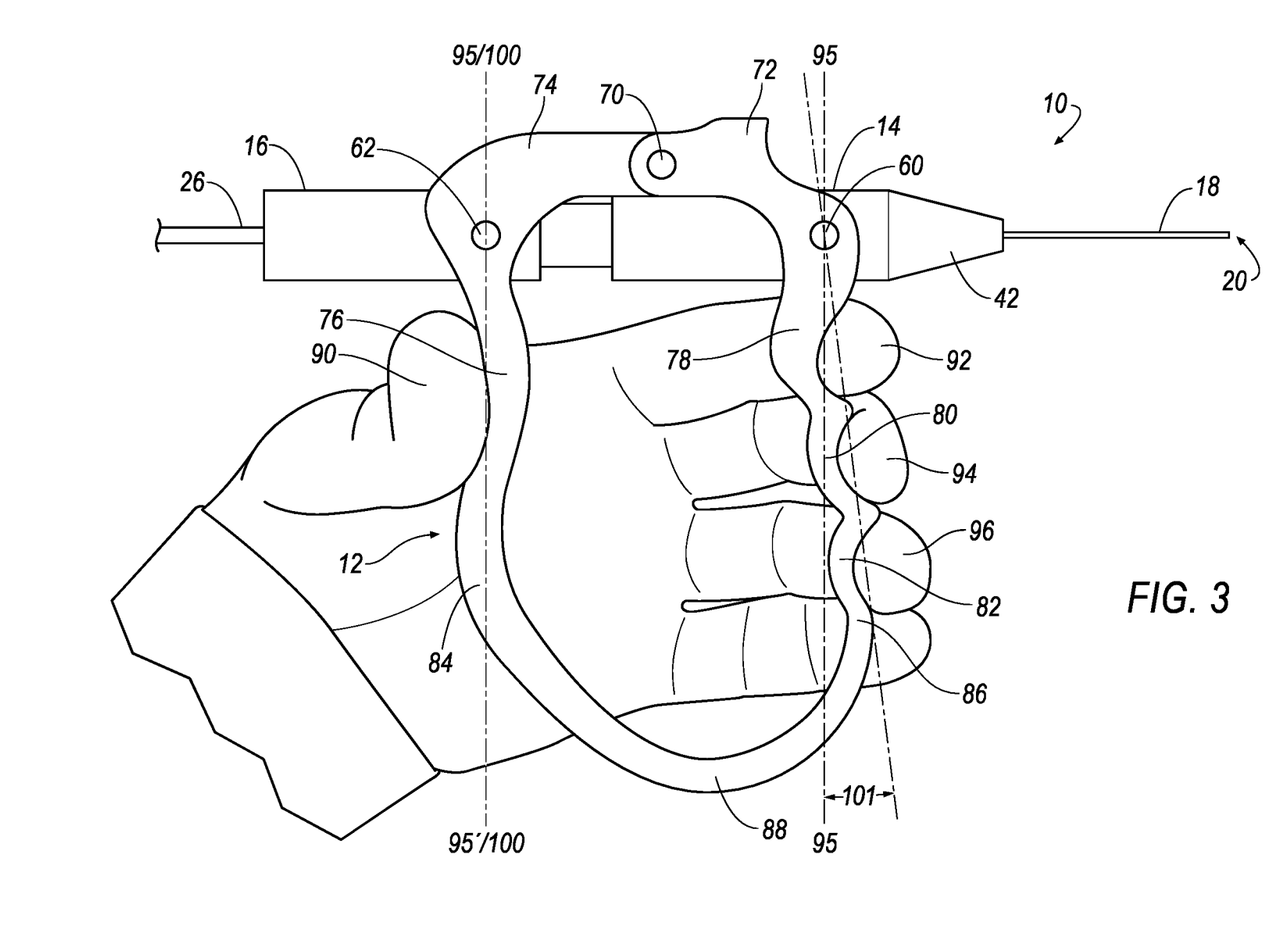
FIG. 3 is a perspective view of a malleable electrosurgical instrument according to one aspect of the invention.

Referring now to FIG. 3, one aspect of the present invention is shown and described. In FIG. 3, electrosurgical handpiece 10 includes the squeezable handle 12 that is comprised generally of materials having at least two different elastic properties. More specifically, squeezable handle 12 includes upper rigid member 72 connected to upper rigid member 74 by fulcrum 70. Pivot 62 connects upper rigid member 74 to the rear body part 16 and acts as a rotational point for the upper rigid member 74. Likewise, pivot 60 connects upper rigid member 72 to front body part 14. Back drip 76 extends downward from pivot 62 and has a concave indentation for placement of the base of the thumb 90 (in one configuration). Likewise, finger grips 78, 80, and 82 extend downward from pivot 60. Each finger grip 78, 80 and 82 is concave for positioning of respective fingers 92, 94 and 96. Notwithstanding the foregoing, it is understood that finger grips 78, 80 and 82 as well as back grip 76 may have no recesses or indentations at all for fingers and the base of the thumb and, instead, can be a relatively straight or other shape sufficient to support a surgeon's hands.

Lower malleable region 88 is made of an elastic material such that the material flexes and bends in response to squeezing of back grip 76 and finger grips 78, 80 and 82 during actuation of the electrosurgical instrument. In one aspect, the elasticity transitions from more rigid to less rigid at transitions 84 and 86.

In FIG. 3, electrosurgical handpiece 10 is shown in the unactuated position. Here, finger grips 78, 80 and 82 generally form a slightly positive angle 101 with respect to a first perpendicular axis 95 relative to common axis 8. A rear angle 100 is approximately equal to a second perpendicular axis 95' relative to the common axis 8. Although not required, this has been shown as a desirable initial first positioning of a surgeon's hands when performing electrosurgical procedures. This position makes it relatively easier for the surgeon to compress and actuate the electrosurgical instrument.

Figure 4:
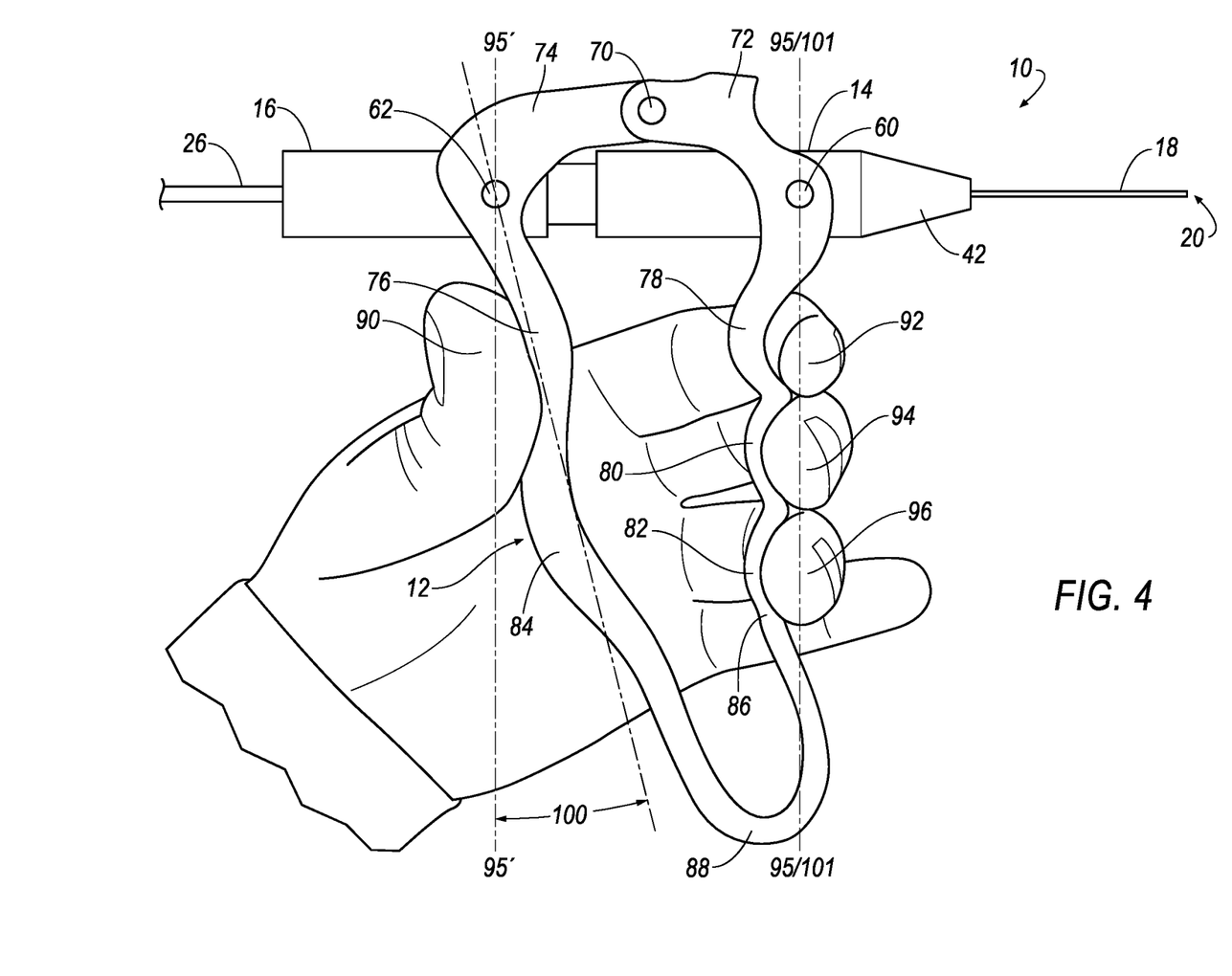
FIG. 4 is a perspective view of a malleable electrosurgical instrument according to one aspect of the invention.

Referring now to FIG. 4, actuation of the electrosurgical handpiece 10 is shown. In this position, the electrosurgical handpiece 10 is shown halfway activated. Here, rear angle 100 is further increased while the front angle 101 is approximately equal to the perpendicular axis. As shown, upper rigid member 72 and upper rigid member 74 rotate about the fulcrum 70. This compresses front body part 14 toward rear body part 16. As shown, lower malleable region 88 flexes and compresses and extends downwardly with respect to the device while the remainder of the squeezable handle 12 remains relatively rigid.

Figure 5:
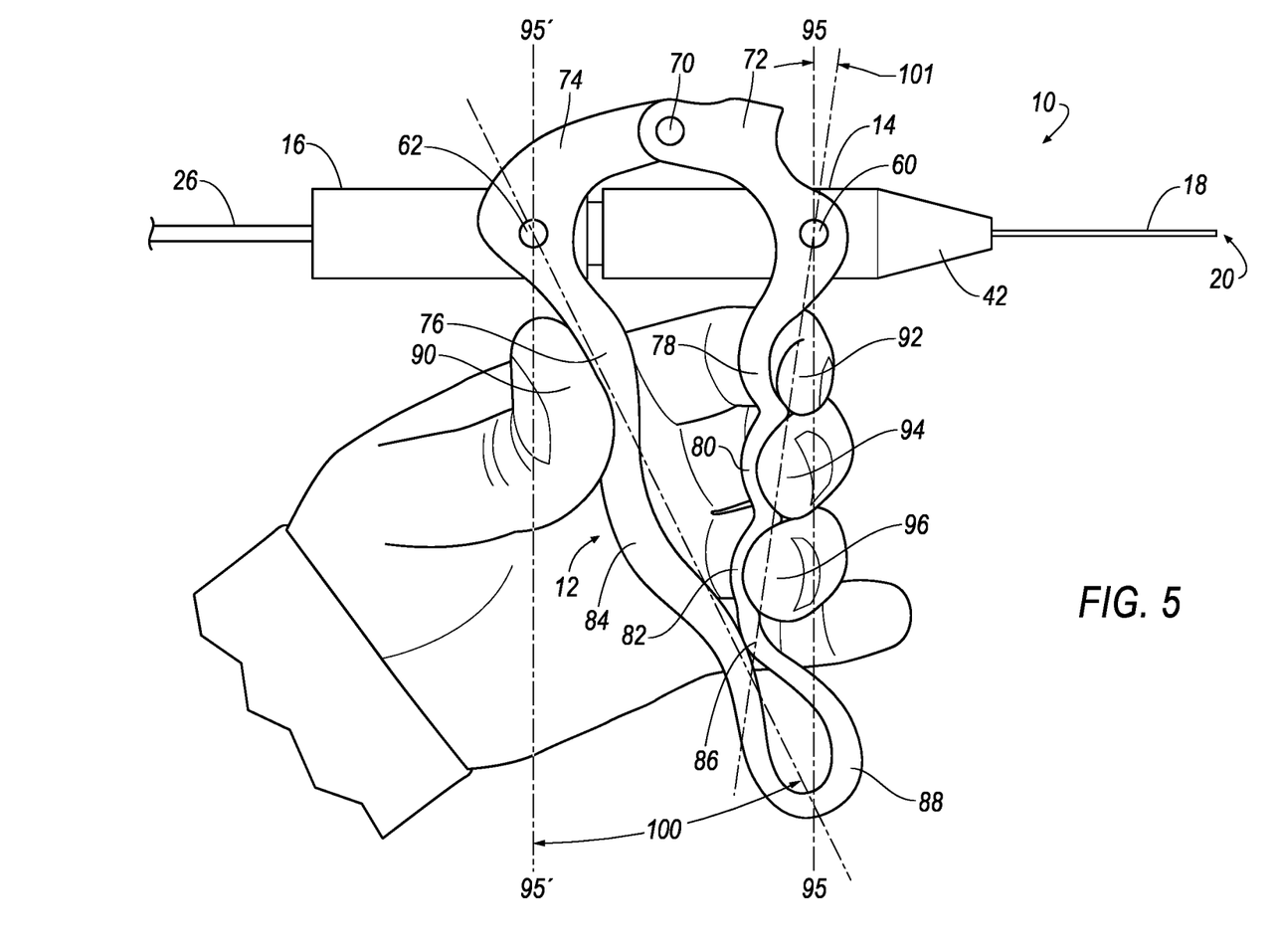
FIG. 5 is a perspective view of a malleable electrosurgical instrument according to one aspect of the invention.

Referring now to FIG. 5, electrosurgical handpiece 10 is shown in its fully actuated position. Here, transition 84 almost or completely touches transition 86. Lower malleable region 88 is fully flexed downwardly as shown in the Figure. Rear angle 100 is further extended while front angle 101 now extends into a negative position with respect to the perpendicular axis relative to the common axis 8.

Upon release, the spring described previously moves the upper rigid member 72 away from upper rigid member 74. In an alternative embodiment, no return spring is provided in the electrosurgical handpiece 10. Instead, lower malleable region 88 has a spring coefficient that sufficiently pushes squeezable handle 12 apart for moving front body part 14 away from rear body part 16. In another embodiment, lower malleable region 88 combines with the spring of electrosurgical handpiece 10 to form a combined spring coefficient to move front body part 14 away from rear body part 16.

Figure 6:
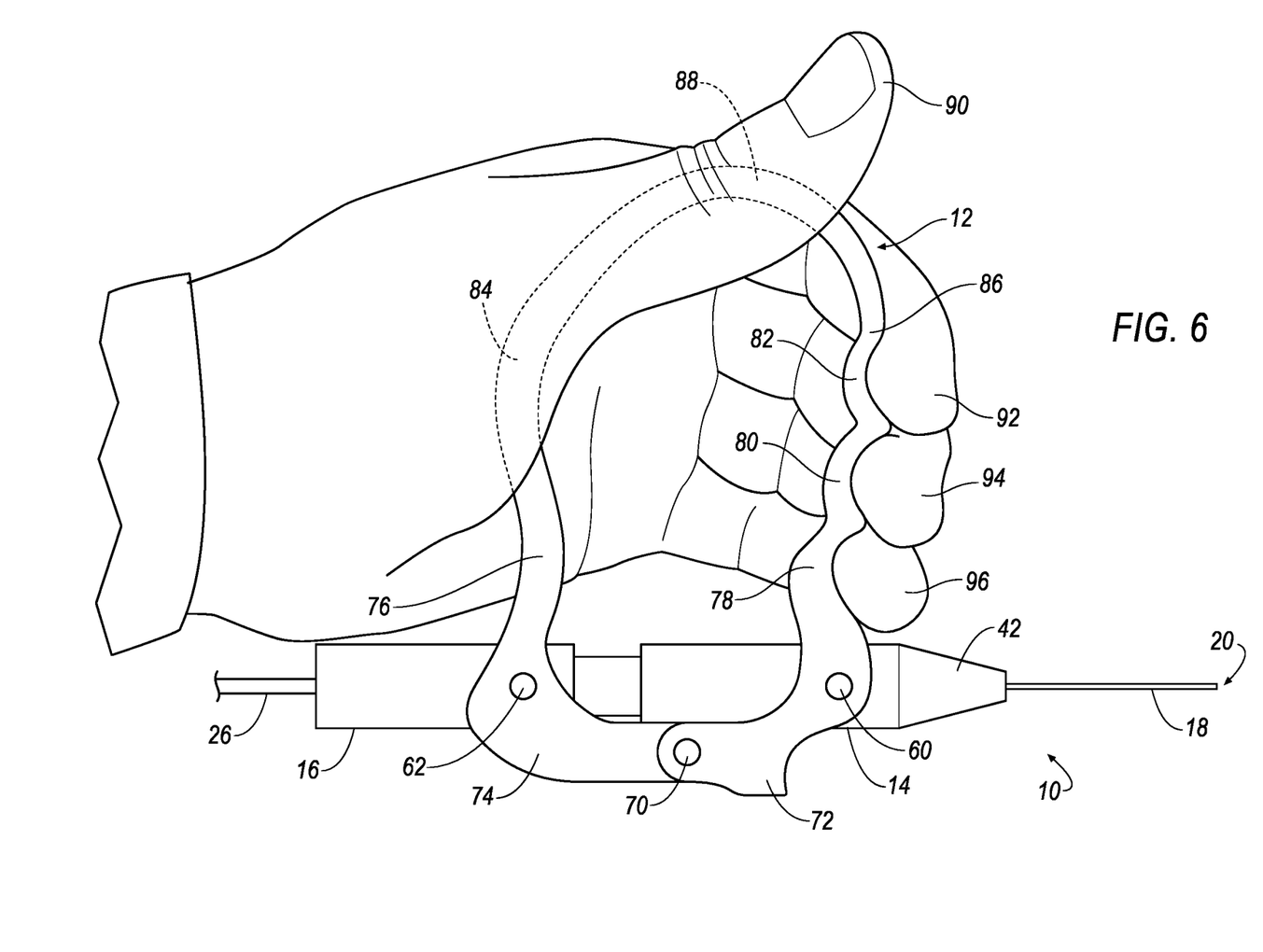
FIG. 6 is a perspective view of a malleable electrosurgical instrument according to one aspect of the invention.
Figure 7:
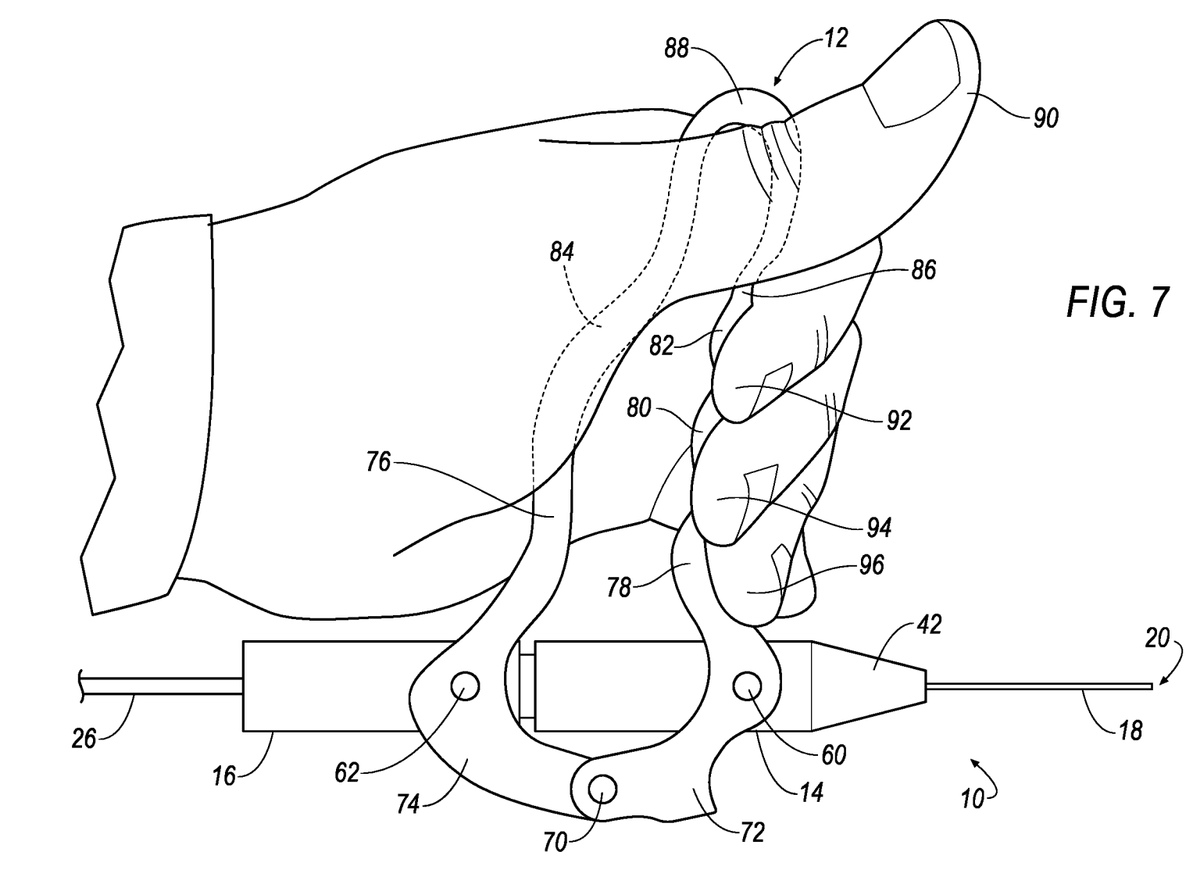
FIG. 7 is a perspective view of a malleable electrosurgical instrument according to one aspect of the invention.

Referring now to FIG. 6 and FIG. 7, another aspect of the present invention is shown and described. In the embodiment of FIG. 6, the electrosurgical instrument 10 is shown being used in an inverted position. Here, the surgeon uses the base of his all with fingers 92, 94 and 96 in opposite positions in finger grips 78, 80 and 82. This inverted position shows, again, advantages associated with the unique configuration of the squeezable handle 12. FIG. 6 shows the electrosurgical handpiece 10 in its on actuated position while FIG. 7 shows electrosurgical handpiece 10 during actuation.

While the invention has been described in connection with preferred embodiments, it will be understood that modifications thereof within the principles outlined above will be evident to those skilled in the art and thus the invention is not limited to the preferred embodiments but is intended to encompass such modifications.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An electrosurgical handpiece for performing surgery, comprising:
   a first body part slidably engaged with a second body part;
   an electrode connected to the first body part;
   a first upper rigid member connected to the first body part at a first pivot;
   a second upper rigid member connected to the second body part at a second pivot,
   wherein the first upper rigid member is connected to the second upper rigid member at a fulcrum disposed above the first and second pivots;
   a back grip extending from the second pivot to which the second upper rigid member is connected;
   a finger grip section extending from the first pivot to which the first upper rigid member is connected;
   a lower malleable, region, wherein: a first end of the lower malleable region connects to a further-most end of the back grip at an end of the back grip that is spaced from and opposite to another end of the back grip that is proximate to the second pivot; and
   a second end of the lower malleable region connects to the finger grip section at a further-most end of the finger grip section that is spaced from and opposite to another end of finger grip section that is proximate to the first pivot; wherein the lower malleable region is more elastic than the first upper rigid member, second upper rigid member, back grip, and finger grip section;
   wherein the first and second upper rigid members both rotate about the fulcrum and about the first and second pivots when the lower malleable region is actuated such that both first and second body parts move toward one another during actuation.

2. The electrosurgical handpiece according to claim 1, wherein: the finger grip section forms a front angle with a first perpendicular axis, wherein the first perpendicular axis is perpendicular to an axis of the electrosurgical handpiece; and the front angle is positive when the electrosurgical handpiece is in an unactuated state.

3. The electrosurgical handpiece according to claim 2, wherein: the back grip forms a back angle with a second perpendicular axis that is perpendicular to the axis of the electrosurgical handpiece, wherein the back angle is negative when the electrosurgical handpiece is in the unactuated state.

4. The electrosurgical handpiece according to claim 3, wherein the back angle is negative when the electrosurgical handpiece is in an actuated state.

5. The electrosurgical handpiece according to claim 4, wherein the front angle is negative when the electrosurgical handpiece is in the actuated state.

6. The electrosurgical handpiece according to claim 1, wherein the lower malleable region has a spring coefficient.

7. The electrosurgical handpiece according to claim 6, wherein the spring coefficient is sufficient to retract the first body part from the second body part when the electrosurgical handpiece is released from an actuated state.

8. The electrosurgical handpiece according to claim 6, wherein the spring coefficient is sufficient to retract the first body part from the second body part in conjunction with another spring element when the electrosurgical handpiece is released from an actuated state.

9. The electrosurgical handpiece according to claim 1, wherein the finger grip section has a plurality of recesses for fitting a respective plurality of fingers.

10. The electrosurgical handpiece according to claim 1, wherein the back grip has at least one recess for a thumb.

11. The electrosurgical handpiece according to claim 1, wherein the second upper rigid member supports the electrode.

12. The electrosurgical handpiece according to claim 1, wherein the electrode is a bipolar electrode.

13. A method for performing surgery with an electrosurgical electrode, comprising:
provided an electrosurgical handpiece with: a first body part slidably engaged with a second body part; a first upper rigid member connected to the first body part at a first pivot; a second upper rigid member connected to the second body part at a second pivot, wherein the first upper rigid member is connected to the second upper rigid member at a fulcrum; a back grip extending from the second pivot of the second upper rigid member; a finger grip extending from the first pivot of the first upper rigid member; wherein the fulcrum is positioned on an opposition side of the first and second body parts than the finger grip and back grip; a lower malleable region, wherein a first end of the lower malleable region connects to the back grip at a further-most end of the back grip, spaced from and opposite to another end of the back grip that is proximate to the second pivot; a second end of the lower malleable region connects the finger grip at a further-most end of the finger grip that is spaced from and opposite to another end of the finger grip that is proximate to the first pivot, thereby connecting the back grip to the finger grip; wherein the lower malleable region is more elastic than the first upper rigid member, second upper rigid member, back grip, and finger grip;
squeezing the finger grip toward the back grip to flex and compress the lower malleable region such that a portion of the lower malleable region extends downwardly with respect to the handpiece to move the first body part and the second body part toward one another to actuate the electrosurgical handpiece.

14. The method according to claim 13, wherein: the finger grip forms a front angle with a first perpendicular axis and an axis of the electrosurgical handpiece; and the front angle is positive when the electrosurgical handpiece is in an unactuated state.

15. The method according to claim 14, wherein: the back grip forms a back angle with the perpendicular axis; wherein the back angle negative when the electrosurgical handpiece is in the unactuated state.

16. The method according to claim 15, wherein the back angle is negative when the electrosurgical handpiece is in an actuated state.

17. The method according to claim 16, wherein the front angle is negative when the electrosurgical handpiece is in the actuated state.

18. An electrosurgical handpiece for performing surgery, comprising:
a first body part slidably engaged with a second body part;
an electrode connected to the first body part;
a first upper rigid member connected to the first body part at a first pivot extending through the first body part;
a second upper rigid member connected to the second body part at a second pivot extending through the second body part,
wherein the first upper rigid member is connected to the second upper rigid member at a fulcrum disposed above the first and second pivots;
a back grip extending from the second pivot to which the second upper rigid member is connected;
a finger grip section extending from the first pivot to which the first upper rigid member is connected;
a lower malleable region, wherein: a first end of the lower malleable region connects to a further-most end of the back grip at an end of the back grip that is spaced from and opposite to another end of the back grip that is proximate to the second pivot; and
a second end of the lower malleable region connects the finger grip section at a further-most end of the finger grip section that is spaced from and opposite to another end of finger grip section that is proximate to the first pivot; wherein the lower malleable region is more elastic than the first upper rigid member, second upper rigid member, back grip, and finger grip section;
wherein the lower malleable region includes a spring coefficient that biases the back grip and the finger grip section apart from one another in the absence of an applied counterforce;
wherein the first and second upper rigid members rotate about the fulcrum and about the first and second pivots when the lower malleable region is actuated.

\* \* \* \* \*